(12) United States Patent
Kim et al.

(10) Patent No.: US 11,801,012 B2
(45) Date of Patent: Oct. 31, 2023

(54) TERMINAL AND METHOD FOR CONTROLLING THE SAME

(71) Applicant: Samsung Display Co., LTD., Yongin-si (KR)

(72) Inventors: Yu Na Kim, Yongin-si (KR); Keum Dong Jung, Yongin-si (KR); Soo Jung Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 507 days.

(21) Appl. No.: 16/886,607

(22) Filed: May 28, 2020

(65) Prior Publication Data

US 2020/0375545 A1 Dec. 3, 2020

(30) Foreign Application Priority Data

Jun. 3, 2019 (KR) ........................ 10-2019-0065398

(51) Int. Cl.
*A61B 5/00* (2006.01)
*A61B 5/05* (2021.01)
*G06F 3/044* (2006.01)

(52) U.S. Cl.
CPC .............. *A61B 5/6898* (2013.01); *A61B 5/05* (2013.01); *A61B 5/4519* (2013.01);
(Continued)

(58) Field of Classification Search
CPC ....... A61B 5/6898; A61B 5/05; A61B 5/4519; A61B 5/4869; A61B 5/4872;
(Continued)

(56) References Cited

U.S. PATENT DOCUMENTS

| 2016/0135741 | A1* | 5/2016 | Chetham | ............... | A61B 5/08 600/391 |
| 2016/0147367 | A1* | 5/2016 | Kim | ................. | A61B 5/332 345/174 |

(Continued)

FOREIGN PATENT DOCUMENTS

| KR | 10-2015-0081735 | 7/2015 |
| KR | 10-1596347 | 2/2016 |

(Continued)

*Primary Examiner* — Eric F Winakur
*Assistant Examiner* — Jonathan Drew Moroneso
(74) *Attorney, Agent, or Firm* — H.C. Park & Associates, PLC

(57) ABSTRACT

The terminal includes a touch panel including first electrodes arranged in a first direction and second electrodes arranged in the second direction intersecting the first direction, a display panel attached to the touch panel and to display an image, and a processor to control the touch panel and the display panel. In a measuring mode, the processor is configured to: apply a driving signal to the touch panel, the touch panel being configured to form an electric field and/or magnetic field when the driving signal is applied, and determine body composition of a user based on a sensing signal output from the touch panel in accordance with eddy current, the eddy current being induced to a body of the user by the electric field and/or magnetic field formed around the touch panel.

7 Claims, 10 Drawing Sheets

(52) U.S. Cl.
CPC .......... *A61B 5/4869* (2013.01); *A61B 5/4872* (2013.01); *A61B 5/4881* (2013.01); *G06F 3/0446* (2019.05)

(58) Field of Classification Search
CPC ... A61B 5/4881; A61B 5/0537; A61B 5/0004; A61B 5/0015; A61B 5/24; G06F 3/0446; H01Q 7/06; H04M 1/725; H04M 2201/34; H04M 2250/22
See application file for complete search history.

(56) References Cited

U.S. PATENT DOCUMENTS

| | | | |
|---|---|---|---|
| 2016/0220143 A1 | 8/2016 | Jung et al. | |
| 2016/0324440 A1 | 11/2016 | Kim et al. | |
| 2016/0367195 A1 | 12/2016 | Park et al. | |
| 2018/0153430 A1* | 6/2018 | Ang | A61B 5/4851 |

FOREIGN PATENT DOCUMENTS

| | | |
|---|---|---|
| KR | 10-2016-0092371 | 8/2016 |
| KR | 10-2016-0094219 | 8/2016 |
| KR | 10-2016-0149878 | 12/2016 |
| KR | 10-1736344 | 5/2017 |

\* cited by examiner

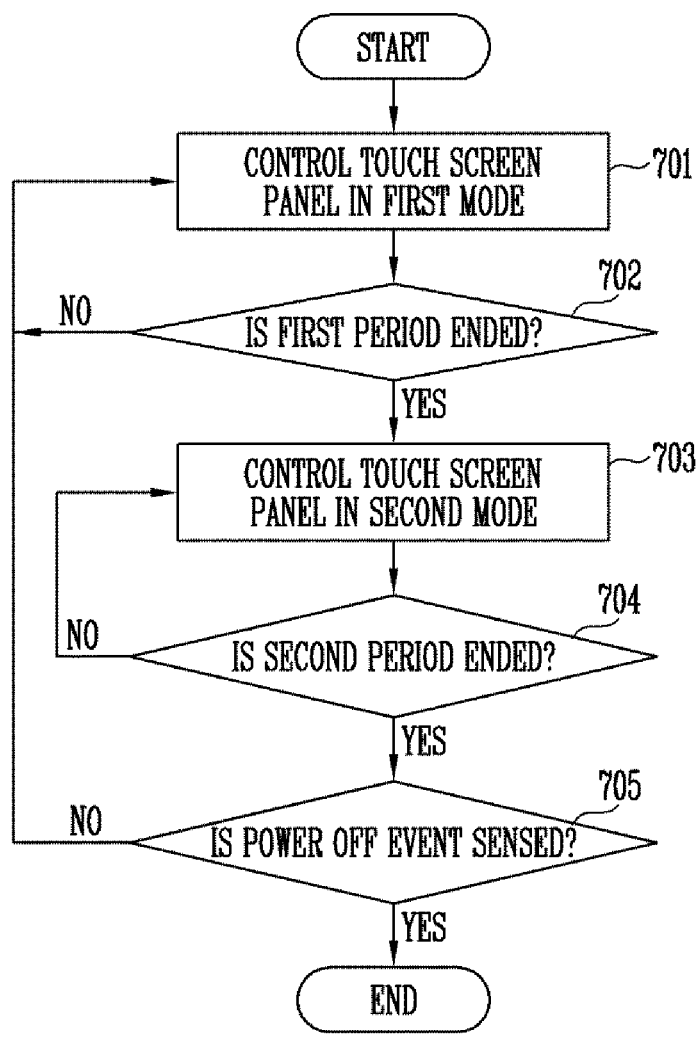

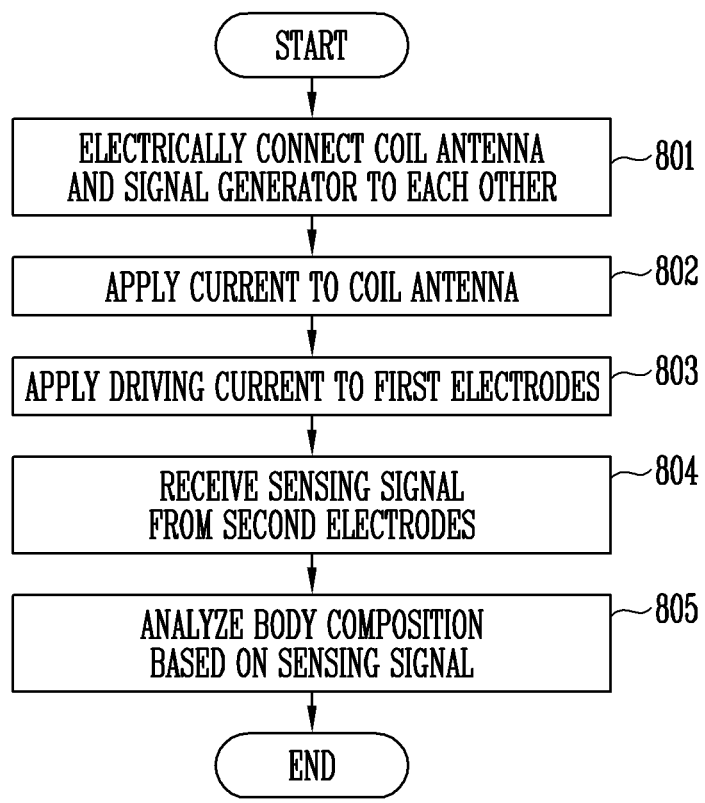
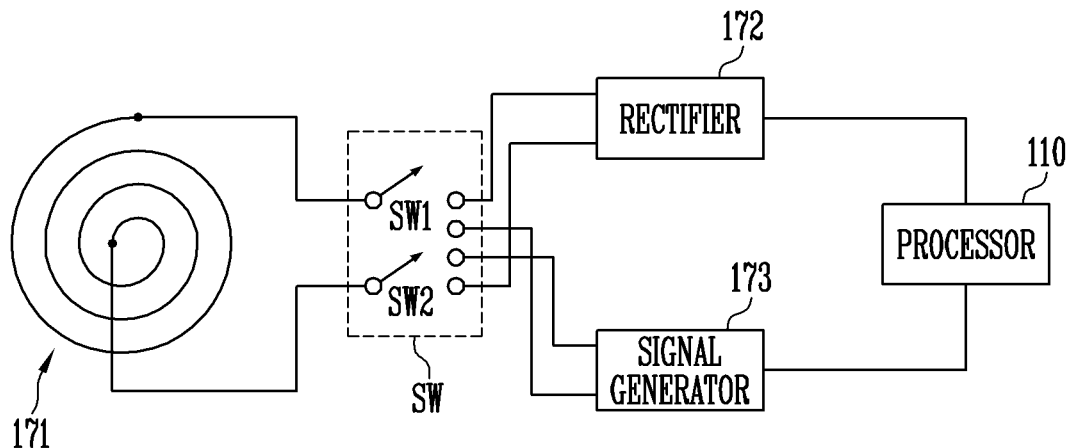

TERMINAL AND METHOD FOR CONTROLLING THE SAME

CROSS REFERENCE TO RELATED APPLICATION

This application claims priority from and the benefit of Korean Patent Application No. 10-2019-0065398, filed on Jun. 3, 2019, which is hereby incorporated by reference for all purposes as if fully set forth herein.

BACKGROUND

Field

Exemplary implementations of the invention relate generally to a terminal and, more specifically, to a terminal capable of measuring a body composition and a method for controlling the terminal for healthcare management.

Discussion of the Background

Recently, various applications for managing health using a terminal such as a smart phone and a tablet PC have been developed. A user may measure body composition such as body fat mass, body water content, and muscle mass using the terminal.

Generally, in order to measure body composition by a terminal, conventional methods use an electrode capable of contacting to the human's body provided integrally or detachably to an outer surface of the terminal.

The above information disclosed in this Background section is only for understanding of the background of the inventive concepts, and, therefore, it may contain information that does not constitute prior art.

SUMMARY

Applicant realized that an external electrode of the terminal to measure body composition is not only detrimental to the terminal aesthetics but also causes problem of dust or moisture damage.

Terminals constructed according to the principles and exemplary implementations of the invention and methods for controlling the same according to the exemplary embodiments of the invention are capable of measuring a body composition of a user by using a coil antenna and a touch screen panel provided inside the terminal without adding a separate hardware configuration. Therefore, the terminal and the method for controlling the terminal according to the exemplary embodiments of the invention may prevent the electrode for measuring the body composition from being exposed to the outside, thereby preventing damage of the electrode and electric shock of the user due to the exposed electrode.

Additional features of the inventive concepts will be set forth in the description which follows, and in part will be apparent from the description, or may be learned by practice of the inventive concepts.

According to one aspect of the invention, a terminal includes: a touch panel including first electrodes arranged in a first direction and second electrodes arranged in the second direction intersecting the first direction, a display panel attached to the touch panel and to display an image, and a processor to control the touch panel and the display panel. In a measuring mode, the processor is configured to: apply a driving signal to the touch panel, the touch panel being configured to form an electric field and/or magnetic field when the driving signal is applied, and determine body composition of a user based on a sensing signal output from the touch panel in accordance with eddy current, the eddy current being induced to a body of the user by the electric field and/or magnetic field formed around the touch panel.

The processor may be configured to apply the driving signal to a first group of the first electrodes and receive the sensing signal from a second group of the first electrodes.

A third group of the first electrodes including at least one first electrode may be disposed between the first group and the second group such that the first group and the second group are spaced apart from each other.

In the measuring mode, the processor may be configured to apply current corresponding to a ground voltage to the third group of the first electrodes, or may not apply current to the third group.

In a sensing mode, the processor may be configured to apply the driving signal to the first electrodes and to sense a touch input based on the sensing signal output from the second electrodes.

The processor may be configured to operate in the measuring mode when a body composition measurement event is sensed while operating in the sensing mode.

The processor may be configured to operate in the sensing mode during a first period and operate in the measuring mode during a second period subsequent to the first period.

According to another aspect of the invention, a terminal includes: a touch panel having a plurality of electrodes, a display panel attached to the touch panel and to display an image, a coil member disposed on a first surface of the display panel, and a processor to control the touch panel, the display panel, and the coil member. In a measuring mode, the processor may be configured to: apply current to the coil member, the coil member being configured to form an electric field and/or magnetic field when the current is applied, and determine body composition of a user based on a sensing signal output from the touch panel in accordance with eddy current, the eddy current being induced to a body of the user by the electric field and/or magnetic field formed around the coil member.

The coil member may include a coil antenna, and the terminal may further include a signal generator to generate an electrical signal of a predetermined frequency, a rectifier to rectify and output a received current, and a switch unit to electrically connect or disconnect between the signal generator, the rectifier, and the coil member.

In the measuring mode, the processor may be configured to control the switch unit electrically connect the signal generator and the coil antenna.

In a sensing mode, the processor may be configured to control the switch unit to electrically connect the rectifier and the coil antenna, and the rectifier may be configured to rectify and output current received from the coil antenna by an induced electromotive force when the induced electromotive force is generated in the coil antenna.

According to still another aspect of the invention, a method for controlling a terminal including a touch panel including first electrodes arranged in a first direction and second electrodes arranged in the second direction intersecting the first direction, the method includes the steps of: applying a driving signal to a first group of either the first electrodes or the second electrodes in a measuring mode, receiving a sensing signal from a second group of either the first electrodes or the second electrodes, and determining a body composition of a user based on the sensing signal.

A third group including at least one first electrode may be disposed between the first group and the second group such that the first group and the second group are spaced apart from each other.

The step of applying the driving signal to the first group may include applying current corresponding to a ground voltage to the third group.

The method may further include the step of determining whether a body composition measurement event is generated before applying the driving signal to the first group, and applying the driving signal to the first group may be performed when the body composition measurement event is generated.

The method may further include the step of applying the driving signal to one of the first electrodes and the second electrodes in a sensing mode when the body composition measurement event is not generated, receiving the sensing signal output from the other of the first electrodes and the second electrodes, and sensing a touch input based on the sensed signal.

The method may further include the step of determining whether a second period corresponding to the measuring mode has elapsed, applying the driving signal to one of the first electrodes and the second electrodes in a sensing mode when the second period has elapsed, receiving the sensing signal output from the other of the first electrodes and the second electrodes, determining whether a first period corresponding to sensing mode has elapsed, and returning to the measuring mode when the first period has elapsed.

According to still another aspect of the invention, a method for controlling a terminal including a touch panel including a plurality of electrodes, and a coil antenna, the method includes the steps of: applying current to the coil antenna in a measuring mode, receiving a sensing signal from the plurality of electrodes, and determining a body composition of a user based on the sensing signal.

The terminal may further include a signal generator to generate an electrical signal of a predetermined frequency, a rectifier to rectify and output a received current, and a switch unit to electrically connect or disconnect between the signal generator, the rectifier, and the coil antenna, and the switch unit may further be controlled to electrically connect the rectifier and the coil antenna before applying the current to the coil antenna.

The method may further include the step of controlling the switch unit to electrically connect the rectifier and the coil antenna in a first mode, and supplying power to the terminal using the current received from the rectifier.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 7 is a flowchart of a method for controlling a terminal according to another exemplary embodiment of the invention.

FIG. 8 is a flowchart of an exemplary embodiment of a method for controlling the terminal in the second mode shown in FIG. 7.

FIG. 9 is a diagram describing an exemplary embodiment of a method for controlling the terminal of FIG. 8.

DETAILED DESCRIPTION

Figure 1:
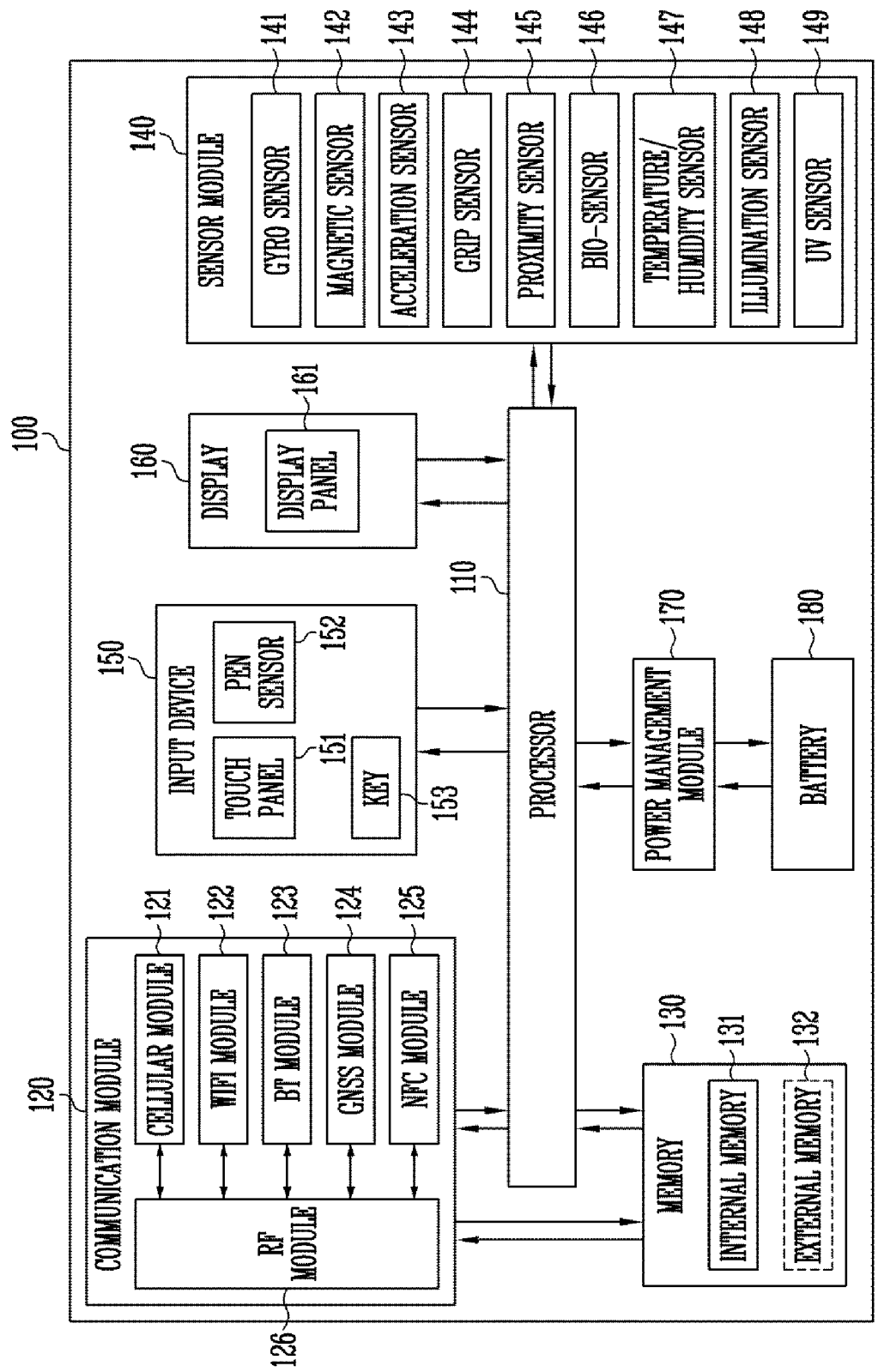
FIG. 1 is a block diagram of an exemplary embodiment of a terminal constructed according to the principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments will be described in more detail with reference to the accompanying drawings. The same or similar reference numerals are used for the same components in the drawings.

A terminal according to various exemplary embodiments may include at least one of a smart phone, a tablet PC, a mobile phone, a video phone, an electronic book reader, a workstation, a PDA, a portable multimedia player ("PMP"), an MP3 player, a medical device, a camera, and a wearable device. A wearable device may include at least one of circuits of an accessory type (for example, a watch, a ring, a bracelet, a bracelet, a necklace, a pair of glasses, a contact lens or a head-mounted device ("HMD")), a fabric or clothing integral type (for example, an electronic clothing), a body attachment type (for example, a skin pad or a tattoo), and a bio-transplantation type.

In an exemplary embodiment, the terminal may include at least one of a television, a digital video disk ("DVD") player, an audio, a refrigerator, an air conditioner, a vacuum cleaner, a microwave oven, an air purifier, a set top box, a home automation control panel, a security control panel, a media box, a game console, an electronic key, a camcorder, and an electronic photo frame.

In another exemplary embodiment, the terminal may include at least one of various medical devices (for example, a portable medical measurement device, a magnetic resonance angiography ("MRA"), a magnetic resonance imaging ("MRI"), a computed tomography ("CT"), an imager, an ultrasonic machine, and the like) a navigation device, an industrial or household robot, and an object Internet device (for example, an electrode, various sensors, a temperature controllers, an exercise device, and the like).

In various exemplary embodiments, the terminal may be a flexible or rigid device. In various exemplary embodiments, the terminal may be a combination of two or more of the various devices described above. However, the terminal is not limited to the above-described devices.

FIG. 1 is a block diagram of an exemplary embodiment of a terminal constructed according to the principles of the invention. Referring to FIG. 1, a terminal 100 may include one or more processors (for example, an AP) 110, a communication module 120, a memory 130, a sensor module 140, an input device 150, a display 160, a power management module 170, and a battery 180.

The processor 110 may drive an operating system or an application program to control various hardware or software components connected to the processor 110. In addition, the processor 110 may perform various data processes and operations required for an operation of the terminal 100.

The processor 110 may be implemented as a system on chip ("SoC"). In an exemplary embodiment, the processor 110 may further include a graphics processing unit ("GPU") and/or an image signal processor. The processor 110 may include at least some of the components shown in FIG. 1 (for example, a cellular module 121). The processor 110 may load and process an instruction or data received from at least one of other components (for example, nonvolatile memory) into a volatile memory and store result data in the nonvolatile memory.

The communication module 120 may configure communication between the terminal 100 and an external device. For example, the communication module 120 may be connected to a network through wireless communication or wired communication to communicate with an external device.

The wireless communication may include a cellular communication using at least one of LTE, LTE advance ("LTE-A"), code division multiple access ("CDMA"), wideband CDMA ("WCDMA"), universal mobile telecommunications system ("UMTS"), wireless broadband ("WiBro") and a global system for mobile communications ("GSM"). In an exemplary embodiment, the wireless communication may include at least one of wireless fidelity ("WiFi"), Bluetooth, Bluetooth low power ("BLE"), Zigbee, near field communication ("NFC"), magnetic secure transmission, radio frequency ("RF"), and a body area network ("BAN"). In an exemplary embodiment, the wireless communication may include a GNSS. The GNSS may be a global positioning system ("GPS"), a global navigation satellite system ("Glonass"), a Beidou navigation satellite system ("Beidou"), or a galileo, the European global satellite-based navigation system.

The wired communication may include at least one of a universal serial bus ("USB"), a high definition multimedia interface ("HDMI"), a recommended standard 232 ("RS-232"), power line communication, or a plain old telephone service ("POTS").

The communication module 120 may include, for example, a cellular module 121, a WiFi module 122, a Bluetooth module 123, a GNSS module 124, an NFC module 125, and an RF module 126.

The cellular module 121 may provide a voice call, a video call, a text service, an Internet service, or the like through a communication network. In an exemplary embodiment, the cellular module 121 may use a subscriber identity module (for example, a SIM card) to perform identification and authentication of the terminal 100 within the communication network.

In an exemplary embodiment, the cellular module 121 may perform at least some of functions that may be provided by the processor 110. In an exemplary embodiment, the cellular module 121 may include a communication processor.

In an exemplary embodiment, at least some of the cellular module 121, the WiFi module 122, the Bluetooth module 123, the GNSS module 124, and the NFC module 125 may be included in one integrated chip ("IC") or an IC package.

The RF module 126 may transmit and receive a communication signal (for example, an RF signal). The RF module 126 may include a transceiver, a power amp module ("PAM"), a frequency filter, a low noise amplifier ("LNA"), an antenna, or the like.

In an exemplary embodiment, at least one of the cellular module 121, the WiFi module 122, the Bluetooth module 123, the GNSS module 124, and the NFC module 125 may transmit and receive the RF signal through a separate RF module.

The memory 130 may include an internal memory 131 or an external memory 132. The internal memory 131 may include at least one of a volatile memory (for example, a DRAM, an SRAM, an SDRAM, or the like), a nonvolatile memory (for example, an one time programmable ROM ("OTPROM"), a PROM, an EPROM, an EEPROM, a mask ROM, a flash ROM, a flash memory, a hard drive, and a solid state drive ("SSD"). The external memory 132 may include a flash drive, for example a compact flash ("CF"), a secure digital ("SD"), a micro-SD, a mini-SD, an extreme digital ("xD"), a memory stick, or the like. The external memory 132 may be functionally or physically connected to the terminal 100 through various interfaces. In various exemplary embodiments, the memory 130 may store at least one algorithm, data, information, and the like necessary for body composition measurement.

The sensor module 140 may measure a physical quantity or sense an operation state of the terminal 100, and convert the measured or sensed information into an electrical signal. The sensor module 140 may include at least one of a gyro sensor 141, a magnetic sensor 142, an acceleration sensor 143, a grip sensor 144, a proximity sensor 145, a bio-sensor 146, a temperature/humidity sensor 147, an illumination sensor 148, and a UV sensor 149. Additionally or alternatively, the sensor module 140 may include an e-nose sensor, an electromyography ("EMG") sensor, an electroencephalogram ("EEG") sensor, an electrocardiogram ("ECG") sensor, an infrared sensor, an iris sensor, and/or a fingerprint sensor.

The sensor module 140 may further include a control circuit for controlling at least one sensor belonging to the sensor module 140. In an exemplary embodiment, the terminal 100 may control the sensor module 140 while the processor 110 is in a sleep state by further including a processor configured to control the sensor module 140 as a part of the processor 110 or separated from the processor 110.

The input device 150 may include a touch panel 151, a (digital) pen sensor 152, or a key 153.

The touch panel 151 may sense a touch input of the user and output a touch event value corresponding to the sensed touch signal. The touch panel 151 may be implemented as a touch screen panel in combination with a display panel 161 described later. In such an exemplary embodiment, the touch panel 151 may be directly disposed on the display panel 161 without a separate base layer. In such an exemplary embodiment, the touch panel 151 may be referred to as a touch sensing unit, an input sensing unit, a touch sensor, or the like.

The (digital) pen sensor 152 may be a part of the touch panel or may include a separate identification sheet. The key 153 may include a physical button, an optical key, or a keypad.

The display 160 may be a liquid crystal display ("LCD"), a light emitting diode ("LED") display, an organic light-emitting diode ("OLED") display, or a microelectromechanical systems ("MEMS") display, or an electronic paper display. The display 160 may include the display panel 161 for displaying various contents (for example, an image, a text, a video, an icon, or a symbol) to the user and control circuitry for controlling the display panel 161.

The display panel 161 may be implemented as a touch screen panel in combination with the touch panel 151. The touch screen may receive a touch, gesture, proximity, or hovering input using a portion of a body of the user. In the following exemplary embodiments, it is assumed that a touch by the body of the user is sensed by using a touch screen panel in which the touch panel 151 and the display panel 161 are integrated.

The power management module 170 may manage power of the terminal 100. In an exemplary embodiment, the power management module 170 may include a power management integrated circuit ("PMIC"), a charge IC, or a battery or fuel gauge.

The PMIC may have a wired and/or wireless charge scheme. The wireless charge scheme may include a magnetic resonance scheme, a magnetic induction scheme, an electromagnetic wave scheme, or the like. The PMIC may include a circuit for wireless charging, for example a coil antenna, a resonance circuit, or a rectifier. When the wireless charge scheme is used, the PMIC may charge the battery 180 using an electromotive force induced to the coil antenna from an external wireless charge device. In various exemplary embodiments, the coil antenna may be used for the wireless charge as well as for measuring the body of the user. Such exemplary embodiments are described in more detail below with reference to the drawings. The battery gauge may measure a remaining amount of the battery 180, a voltage, current, or a temperature during charging.

The battery 180 may include a rechargeable battery and/or a solar cell.

Figure 2:
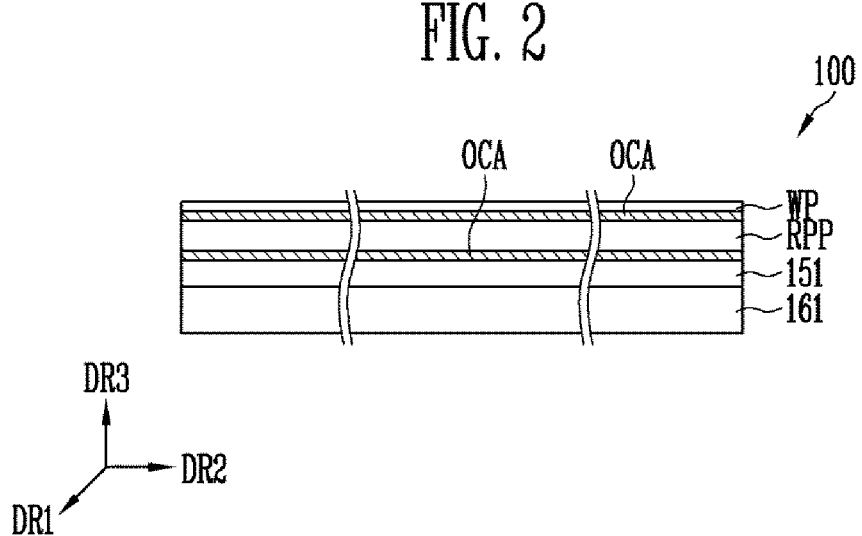
FIG. 2 is a schematic side view of an exemplary embodiment of a terminal constructed according to the principles of the invention.
Figure 3:
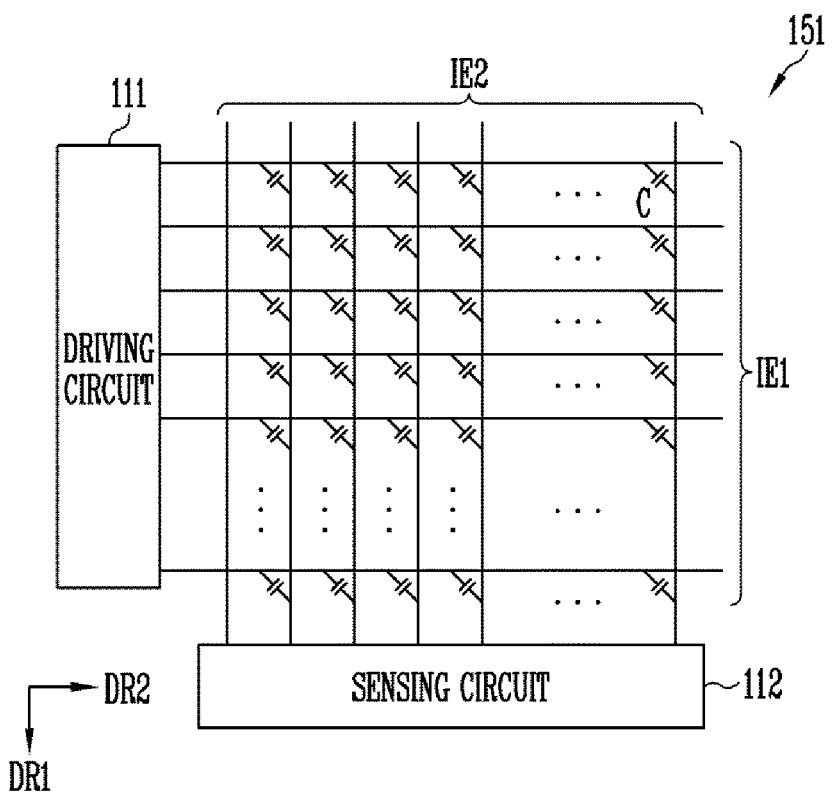
FIG. 3 is a plan view of an exemplary embodiment of the touch panel shown in FIG. 2.

FIG. 2 is a schematic side view of an exemplary embodiment of a terminal according to the principles of the invention. FIG. 2 is schematically shown to describe a stack relationship of functional panels and/or functional units configuring the terminal 100. FIG. 3 is a plan view of an exemplary embodiment of the touch panel shown in FIG. 2.

Referring to FIG. 2, the terminal 100 may include the display panel 161 and the touch panel 151. The display panel 161 and the touch panel 151 may be coupled to each other to form a touch screen panel.

The terminal 100 may further include an antireflection layer RPP and a window WP. Configurations of at least some of the display panel 161, the touch panel 151, the antireflection layer RPP, and the window WP may be formed by a continuous process or may be coupled to each other through an adhesive member OCA.

In FIG. 2, an optical transparent adhesive member is exemplarily illustrated as an adhesive member OCA, but the technical spirit of the disclosure is not limited thereto, and a normal adhesive may be used as the adhesive member OCA. The antireflection layer RPP and window WP may be replaced with different configurations or may be omitted.

The display panel 161 may display an image. The display panel 161 may be a light emitting type display panel, but is not limited thereto. For example, the display panel 161 may be an organic light emitting display panel or a Quantum dot light emitting display panel. A light emitting layer of the organic light emitting display panel may include an organic light emitting material. A light emitting layer of the Quantum dot light emitting display panel may include a quantum dot, a quantum rod, and the like.

The touch panel 151 senses user touch. For example, the touch panel 151 may obtain coordinate information in which the touch is input.

The touch panel 151 may be directly disposed on the display panel 161. In various exemplary embodiments, a sentence "a configuration of B is directly disposed on a configuration of A." may mean that a separate adhesive layer/adhesive member is not disposed between the configuration of A and the configuration of B. For example, the configuration of B may be formed through a continuous process on a base surface provided by the configuration of A after the configuration of A is formed. In such an exemplary embodiment, the touch panel 151 may be referred to as a touch sensing unit, an input sensing unit, a touch sensor, or the like. When the touch panel 151 is directly disposed on the base surface provided by the display panel 161, a separate base layer may be omitted from the touch panel 151, and thus reducing the thickness of the terminal 100.

However, the exemplary embodiment is not limited thereto. That is, in various exemplary embodiments, the touch panel 151 may be implemented as a panel including a base layer and may be attached on the display panel 161 through an adhesive layer. The base layer may include, for example, a synthetic resin film, a composite material film, a glass substrate, or the like.

In various exemplary embodiments, the touch panel 151 may include electrodes IE (e.g., IE1 and IE2), signal lines connected to the electrodes IE, and at least one insulating layer for insulating between the electrodes IE and/or the signal lines. The electrodes IE may include first electrodes IE1 and second electrodes IE2 arranged to cross each other as shown in FIG. 3. For example, the first electrodes IE1 are arranged in a first direction DR1 and each of the first electrodes IE1 extends in a second direction DR2. The second electrodes IE2 are arranged in the second direction DR2 and each of the second electrodes IE2 extends in the first direction DR1.

In an exemplary embodiment, the first electrodes IE1 may operate as driving electrodes, and the second electrodes IE2 may operate as sensing electrodes. Alternatively, the first electrodes IE1 may operate as sensing electrodes, and the second electrodes IE2 may operate as driving electrodes. The driving electrodes may be electrically connected to a driving circuit, and the sensing electrodes may be electrically connected to a sensing circuit. A driving circuit 111 and a sensing circuit 112 may be provided in at least one of the display panel 161 and the processor 110. Alternatively, a portion of the driving circuit 111 and the sensing circuit 112 may be provided in the display panel 161 and the remaining portion may be provided in the processor 110. The driving circuit 111 and the sensing circuit 112 may be provided separately from each other or at least partly integrated.

The driving electrodes may receive a driving signal from the driving circuit 111. In an exemplary embodiment, the driving electrodes may be supplied with the driving signals simultaneously or sequentially. In various exemplary embodiments, only a portion of the driving electrodes may receive the driving signal according to a mode of the terminal 100.

When the driving signal is applied to the driving electrodes, a sensing signal corresponding to the driving signal is output from each of the sensing electrodes by a coupling of a capacitance C. For example, when the touch input is applied to the touch panel 151, the sensing signal from the sensing electrode located adjacent to the touch input may be input to the sensing circuit 112.

In the above description, an exemplary embodiment in which the touch panel 151 senses the touch input by the capacitive method. However, the exemplary embodiment is not limited thereto, and in various exemplary embodiments, the touch panel 151 may sense the touch input or the like by an electromagnetic induction method or a pressure sensing method.

The capacitive method for sensing the touch input may include a mutual cap method and a self-cap method. For example, the electrodes IE may sense the touch input in the mutual cap method and/or the self-cap method. Alternatively, the electrodes IE may sense the touch input during a first period with the mutual cap method and may sense the touch input during a second period subsequent to the first period with the self-cap method.

Meanwhile, in FIG. 3, although the electrodes IE are shown in an extended line form, the exemplary embodiment is not limited thereto. That is, in various exemplary embodiments, each of the electrodes IE may be configured of sensor portions of a polygon (for example, a rhombus), and connection portions connecting the sensor portions to each other. In such an exemplary embodiment, the sensor portions of the first electrodes IE1 and the sensor portions of the second electrode IE2 may be formed on the same layer among a plurality of layers included in the touch panel 151. At this time, the connection portions of the first electrodes IE1 and the connection portions of the second electrodes IE2 may cross each other. Here, any one of the connection portions of the first electrodes IE1 and the connection portions of the second electrodes IE2 may be provided in a bridge structure disposed on a different layer and may connect the sensor portions to each other. A shape and a configuration method of the electrodes IE are not particularly limited.

In various exemplary embodiments, the touch panel 151 may further be used for body measurement of a user. When an electric field is formed around the terminal 100 by the driving electrode to which current is applied or a coil member such as a coil antenna 171 of FIGS. 4 and 5 described later or the like, eddy current may be induced to a body of the user approaching the terminal 100. Therefore, a coupling of the capacitance C corresponding to the eddy current may occur between the driving electrode (e.g., IE1) and the sensing electrode (e.g., IE2). That is, the eddy current may affect the capacitance C between the driving electrode (e.g., IE1) and the sensing electrode (e.g., IE2). As such, a sensing signal according to the coupling of the capacitance C may be output from the touch panel 151. The eddy current induced to the body of the user may change according to the body composition of the users, respectively. The body composition may include at least one of, for example, body fat mass, body water mass, muscle mass, protein mass, and inorganic mass. Therefore, the body composition of the user may be analyzed based on the change of the capacitance C sensed by the touch panel 151.

The antireflection layer RPP reduces a reflectance of external light incident from above the window WP. The antireflection layer RPP may include a phase retarder and a polarizer. The phase retarder may be a film type or a liquid crystal coating type, and may include a λ/2 phase retarder and/or a λ/4 phase retarder. The polarizer may also be a film type or a liquid crystal coating type. The film type may include a stretch-type synthetic resin film, and the liquid crystal coating type may include liquid crystals arranged in a predetermined arrangement. The phase retarder and the polarizer may further include a protective film. The phase retarder and the polarizer or the protective film may be defined as a base layer of the antireflection layer RPP.

The window WP may be provided to protect lower layers from external dust or moisture. The window WP may include an organic substrate, a synthetic resin film, and/or the like. The window WP may further include a functional coating layer such as an anti-fingerprint layer, an antireflection layer, and a hard coating layer.

In an exemplary embodiment, a single layer or multi-layer protective member may be provided under the display panel 161. The protective member and the display panel 161 may be coupled through an adhesive member.

Figure 4:
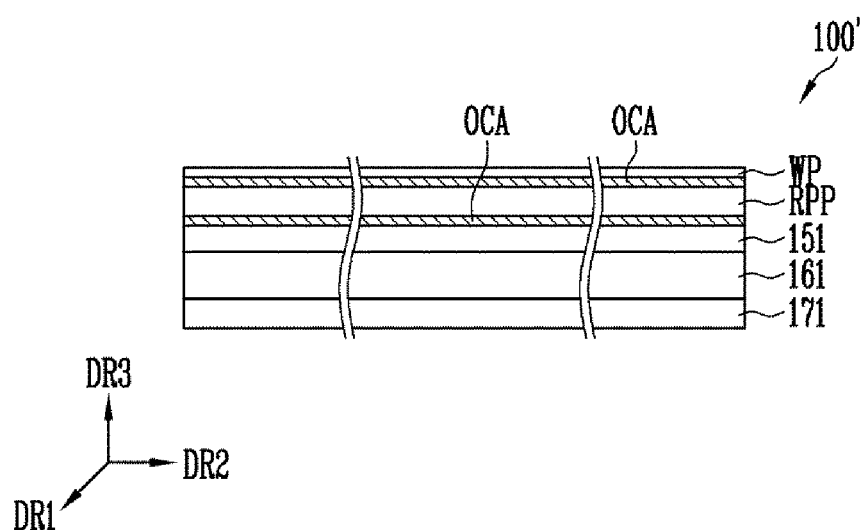
FIG. 4 is a schematic side view of another exemplary embodiment of a terminal constructed according to the principles of the invention.
Figure 5:
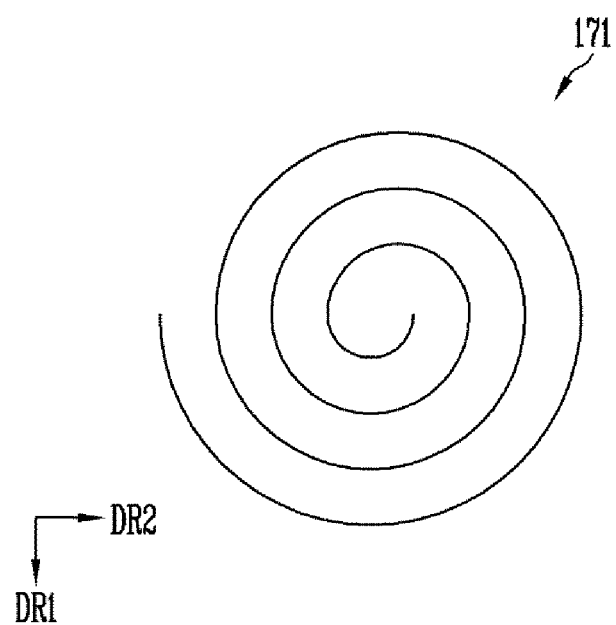
FIG. 5 is a plan view of an exemplary embodiment of the coil antenna shown in FIG. 4.

FIG. 4 is a schematic side view of another exemplary embodiment of a terminal constructed according to the principles of the invention. FIG. 5 is a plan view of another exemplary embodiment of the coil member such as the coil antenna shown in FIG. 4.

The terminal 100' shown in FIG. 4 is substantially the same as the terminal 100 shown in FIG. 2 except that the terminal 100' further includes a coil member such as coil antenna 171 as compared with the terminal 100 shown in FIG. 2. Therefore, in describing the terminal 100' shown in FIG. 4, the same reference numerals are given to the same or similar components as those of the terminal 100 shown in FIG. 2, and a detailed description thereof will be omitted.

The coil antenna 171 may be provided inside the terminal 100' as shown in FIG. 4. In an exemplary embodiment, the coil antenna 171 may be disposed under the display panel 161 in the terminal 100'.

The coil antenna 171 may have a ring shape as shown in FIG. 5, but is not limited thereto, and may have a spiral, a loop, or a meander shape. In addition, the coil antenna 171 may be an air-core coil or a core type coil according to a component. The air-core coil is a coil that maintains the inside of a cylinder empty by winding an electric wire and has no magnetic core in the center, and is configured so that electric flows around an empty cylinder axis. The core coil is a rod-shaped or E-shaped coil in which a winding wire is wound around a drum core.

In an exemplary embodiment, an induced electromotive force may be generated in the coil antenna 171 by an external wireless charge device or the like. A rectifier 172 shown in FIG. 9 electrically connected to the coil antenna 171 may rectify a received current according to the induced electromotive force generated in the coil antenna 171 to supply power to the battery 180 and the like. Accordingly, the coil antenna 171 may be used for wireless charging.

In various exemplary embodiments, the coil antenna 171 may be further used for the body measurement of the user in addition to wireless charging. In such an exemplary embodiment, the coil antenna 171 may receive current having a predetermined magnitude and/or frequency (i.e., predetermined AC current) from a signal generator 173 shown in FIG. 9 or the like connected to the coil antenna 171. The current applied to the coil antenna 171 may form an electric field around the coil antenna 171. The formed electric field may induce the eddy current in the body of the user approaching the terminal 100', which may determine degree of change of the capacitance C sensed by the touch panel 151. The eddy current induced to the body of the user may change according to the body composition of the user. The body composition may include at least one of, for example, body fat mass, body water mass, muscle mass, protein mass, and inorganic mass. Therefore, the body composition of the user may be analyzed based on the change of the capacitance C sensed by the touch panel 151.

The coil antenna 171 may be electrically connected to the rectifier 172 shown in FIG. 9 or the like, or may be electrically connected to a signal generator 173 shown in FIG. 9 or the like according to an operation state of the coil antenna 171. To this end, a switching element SW shown in FIG. 9 for controlling the electrical connection between the coil antenna 171, rectifier or the like, and the signal generator 173 or the like may be provided. The switching element SW may be controlled by the processor 110, but the disclosure is not limited thereto.

In FIG. 4, the coil antenna 171 used for the wireless charging is described as a representative exemplary embodiment, but the exemplary embodiment is not limited thereto. That is, the coil antenna 171 shown in FIG. 4 may be another coil provided in the RF antenna, the (digital) pen sensor 152, or the like, or may be replaced with these.

Hereinafter, a method for controlling the terminal, which includes the above-described body composition measurement of the user will be described in more detail.

Figure 6:
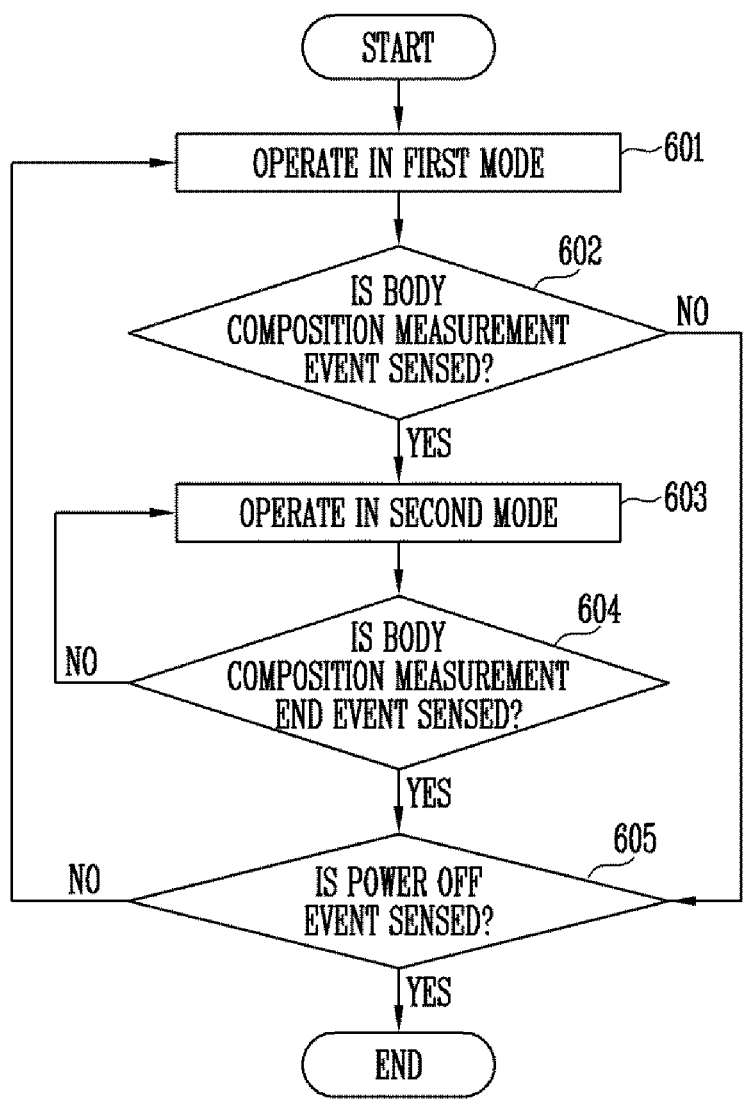
FIG. 6 is a flowchart of a method for controlling a terminal according to an exemplary embodiment of the invention.

FIG. 6 is a flowchart of a method for controlling terminal according to an exemplary embodiment of the invention.

Referring to FIG. 6, the terminal 100 may operate in a first mode (601). The first mode may be, for example, a normal operation state of the terminal 100, and may include a standby mode.

In the first mode, the touch screen panel may operate so as to sense the touch input of the user. For example, in the first mode, the driving signal may be applied to the first electrodes IE1 of the touch panel 151, and the sensing signal output from the second electrodes IE2 may be analyzed. That is, the first mode may correspond to a first period to sense the touch input of the user. As such, the first mode may be a sensing mode.

In addition, in the first mode, the coil antenna 171 may be controlled so as to supply power to the terminal 100 according to whether the coil antenna 171 is electrically coupled with a wireless charge device or the like. For example, in the first mode, the coil antenna 171 may be connected to the rectifier or the like, and when the induced electromotive force is generated by the wireless charge device or the like, the coil antenna 171 may transmit the generated induced electromotive force to the rectifier or the like.

While operating in the first mode, the terminal 100 may sense a body composition measurement event (602). The body composition measurement event may occur by execution of an application related to the body composition measurement, a user input corresponding to a body composition measurement request, a touch input at two or more points of the touch screen panel, and the like. Here, the user input may be generated through an application related to the body composition measurement, or may be sensed by the input device 150 or the like provided in the terminal 100.

When the body composition measurement event is sensed, the terminal 100 may operate in a second mode (603). The second mode may include, for example, a body composition measurement performance state. That is, the second mode may correspond to a second period to measure the body composition of the user. As such, the second mode may be a measuring mode.

In the second mode, the terminal 100 may measure the body composition of the user through the touch screen panel. For example, the processor 110 may supply the driving signal to a first group of first electrodes IE1 in the touch panel 151 and receive the sensing signal output from a second group of first electrodes IE1. The processor 110 may determine the change of the capacitance C between the first electrodes IE1 of the first group and the first electrodes IE1 of the second group based on the sensing signal and analyze the body composition based on the determined capacitance C. For example, when an electric field is formed around the terminal 100 by supplying the driving signal to the first group of first electrodes IE1, eddy current may be induced to a body of the user approaching the terminal 100. Thus, a coupling of the capacitance C corresponding to the eddy current may occur between the first group of first electrodes IE1 (i.e., driving electrode) and the second group of first electrodes IE1 (i.e., sensing electrode). That is, the eddy current may affect the capacitance C between the driving electrode (e.g., IE1) and the sensing electrode (e.g., IE2). As such, the sensing signal according to the coupling of the capacitance C may be output from the touch panel and the processor 110 may analyze the body composition based on the determined capacitance C.

In another exemplary embodiment, the terminal 100 may measure the body composition using the second electrodes IE2 in the touch panel 151. That is, the processor 110 may supply the driving signal to a first group of the second electrodes IE2 in the touch panel 151 and receive the sensing signal output from a second group of the second electrodes IE2. The u) processor 110 may determine the change of the capacitance C between the second electrode IE2 of the first group and the second electrode IE2 of the second group based on the sensing signal and analyze the body composition based on the determined capacitance C.

Alternatively, in the second mode, the terminal 100 may measure the body composition of the user through the coil antenna 171 and the touch screen panel. For example, the processor 110 may apply current having a predetermined magnitude and/or frequency (i.e., predetermined AC current) to the coil antenna 171. The current applied to the coil antenna 171 may form an electric field around the coil antenna 171. The formed electric field may induce the eddy current in the body of the user approaching the terminal. In addition, the processor 110 may supply the driving signal to the driving electrodes (e.g., IE1) in the touch panel 151 and receive the sensing signal output from the sensing electrodes (e.g., IE2). The processor 110 may determine the change of the capacitance C between the driving electrodes and the sensing electrodes based on the sensing signal and analyze the body composition based on the determined capacitance C. In such an exemplary embodiment, the coil antenna 171 may generate a magnetic field in place of the electrode receiving the driving signal in the above-described exemplary embodiment.

When the body composition is measured in a different manner as described above, the terminal 100 may derive the body composition from the change of the capacitance C by a different algorithm. A method of measuring the body composition of the terminal 100 in the second mode will be described in more detail below.

The terminal 100 may sense a body composition measurement end event (604). The body composition measurement end event may be generated by completion of the body composition measurement, a user input corresponding to a body composition measurement end request, an end of at least one touch input at two or more points of the touch screen panel, and the like. Here, the user input may be generated through an application related to the body composition measurement, or may be sensed by the input device 150 or the like provided in the terminal 100. Here, the user input may be generated through an application related to body composition measurement, or may be sensed by the input device 150 provided in the terminal 100 or the like.

When the body composition measurement end event is sensed, the terminal 100 may operate in the first mode again (601).

The terminal 100 may repeatedly perform the above-described operation until a power off event by a power supply interruption, a user input, or the like is sensed (605). FIG. 6 shows that the terminal 100 determines whether the power off event is sensed while the terminal 100 operates in the first mode or after the body composition measurement end event is sensed, but the exemplary embodiment is not limited thereto. That is, the terminal 100 may end the above-described operations when the power off event is sensed at any time while the terminal 100 operates in the second mode or while the terminal 100 performs the operation shown in FIG. 6.

FIG. 7 is a flowchart of a method for controlling a terminal according to another exemplary embodiment of the invention.

Referring to FIG. 7, during a first period, the terminal 100 may control the touch screen panel in the first mode (701). Specifically, the processor 110 may control the touch screen panel to operate for touch input sensing in the first mode. That is, the first mode may correspond to the first period to sense the touch input of the user. As such, the first mode may be a sensing mode.

In the first mode, the processor 110 may apply the driving signal to the driving electrodes of the touch panel 151, for example, the first electrodes IE1, and may receive the sensing signal output from the sensing electrodes, for example, the second electrodes IE2. The processor 110 may sense the touch input by analyzing the received sensing signal.

When the first period ends (702), the terminal 100 may control the touch screen panel in the second mode during a second period (703). Specifically, the processor 110 may control the touch screen panel to operate for the body composition measurement in the second mode. That is, the second mode may correspond to the second period to measure the body composition of the user. As such, the second mode may be a measuring mode.

In the second mode, the processor 110 may supply the driving signal to the first group of the first electrodes IE1 in the touch panel 151 and receive the sensing signal output from the second group of the first electrodes IE1. The processor 110 may determine the capacitance C between the first electrodes IE1 of the first group and the first electrodes IE1 of the second group based on the sensing signal and analyze the body composition based on the determined capacitance C.

In another exemplary embodiment, the terminal 100 may measure the body composition using the second electrodes IE2 in the touch panel 151. That is, the processor 110 may supply the driving signal to the first group of the second electrodes IE2 in the touch panel 151 and receive the sensing signal output from the second group of the second electrodes IE2. The processor 110 may determine the capacitance C between the second electrode IE2 of the first group and the second electrode IE2 of the second group based on the sensing signal and analyze the body composition based on the determined capacitance C.

When the second period ends (704), the terminal 100 may control the touch screen panel in the first mode again during the first period (701).

The terminal 100 may repeatedly perform the above-described operation until a power off event by a power supply interruption, a user input, or the like is sensed (705). FIG. 7 shows that the terminal 100 determines whether the power off event is sensed after the second period, but the exemplary embodiment is not limited thereto. That is, the terminal 100 may end the above-described operations when the power off event is sensed at any time during the first period or during the operation shown in FIG. 7.

Such an exemplary embodiment may be applied to the terminal 100 in which the coil antenna 171 is not provided as shown in FIG. 2. However, the exemplary embodiment is not limited thereto, and such an exemplary embodiment may also be applied to the terminal 100' in which the coil antenna 171 is provided as shown in FIG. 4. In such an exemplary embodiment, the coil antenna 171 may be used only for wireless charging, or may be used further for other functions except for the body composition measurement. Alternatively, in such an exemplary embodiment, the coil antenna 171 may be used for the body composition measurement instead of or in addition to a touch screen pad as occasion demands.

Meanwhile, in various exemplary embodiments, the touch panel 151 may sense the touch input in the mutual cap method during the first period, that is, in the first mode, and may sense the touch input in the self-cap method during the second period, that is, in the second mode. However, the exemplary embodiment is not limited thereto.

FIG. 8 is a flowchart of an exemplary embodiment of a method for controlling the terminal in the second mode shown in FIG. 7. FIG. 9 is a diagram describing an exemplary embodiment of a method for controlling the terminal of FIG. 8. FIGS. 8 and 9 show a method of measuring the body composition using the coil antenna 171 and the touch screen panel.

Referring to FIG. 9, before operation in the second mode, that is, in the first mode, the coil antenna 171 may be electrically connected to the rectifier 172 by turning on a first switch SW1 and turning off a second switch SW2. The rectifier 172 may receive current induced to the coil antenna 171 and may pass current of a specific frequency band through resonance. The current output through the rectifier 172 may further be controlled through another control circuit or the like configuring the PMIC and may be supplied to a power demand such as the battery 180.

Referring to FIGS. 8 and 9, in the second mode, the processor 110 may electrically connect the coil antenna 171 to the signal generator 173 (801) by turning on the second switch SW2 and turning off the first switch SW1. That is, the processor 110 may apply current to the coil antenna 171.

The processor 110 may controls the switch unit SW disposed between the coil antenna 171, the rectifier 172, and the signal generator 173 to electrically disconnect between the coil antenna 171 and the rectifier 172 by turning off the first switch SW1 and electrically connect between the coil antenna 171 and the signal generator 173 turning on the second switch SW2. Therefore, the current may be applied to the coil antenna 171 through the signal generator 173.

The processor 110 may apply the current to the coil antenna 171 through the signal generator 173 (802). In an exemplary embodiment, the signal generator 173 may include an oscillator that generates an electrical signal of a predetermined frequency. Alternatively, the signal generator 173 may include a pulse width modulation ("PWM") and a DC-AC converter that generate an electrical signal of a predetermined frequency. Therefore, a DC signal generated by the PWM may be converted into an AC signal of a predetermined frequency through the DC-AC converter.

In the second mode, the frequency of the AC signal applied to the coil antenna 171 may be set to a value suitable for the body composition measurement. For example, the frequency of the AC signal applied to the coil antenna 171 in the second mode may be at least one of frequencies in a range of several tens of kHz to several MHz. In an exemplary embodiment, the frequency of the AC signal may be at least one of 50 kHz, 125 kHz, and 250 kHz, but the disclosure is not limited thereto. In various exemplary embodiments, the frequency of the AC signal applied to the coil antenna 171 may vary according to a kind of the body composition to be measured.

When the AC signal is applied to the coil antenna 171, an electric field (and/or a magnetic field) may be formed around the coil antenna 171. The electric field around the coil antenna 171 may induce an eddy current to the body of the user approaching the terminal 100.

The processor 110 may apply the driving current to the driving electrodes of the touch panel 151 provided in the touch screen panel, for example, the first electrodes IE1 (803). The driving current may be applied to the first electrodes IE1 before the coil antenna 171 and the signal generator 173 are electrically connected to each other. In various exemplary embodiments, the driving current may be simultaneously applied to the first electrodes IE1. Since it may not be determined the position at which the body is in contact with the touch panel 151 at the time of the body composition measurement, the driving current may be simultaneously applied to the first electrodes IE1 instead of sequentially applied to the first electrodes IE1. However, the exemplary embodiment is not limited thereto.

The processor 110 may receive the sensing signal output from the sensing electrodes of the touch panel 151 provided in the touch screen panel, for example, the second electrodes IE2 (804). The processor 110 may analyze the body composition of the user based on the sensing signal (805).

The sensing signal may include information of the capacitance C formed between the first electrodes IE1 and the second electrodes IE2. The capacitance C may vary according to an electrical characteristic of the body of the user who is in contact with the touch screen panel and the electrical characteristic of the body of the user may be determined according to the eddy current induced by the electric field of the coil antenna 171. The eddy current may vary based on the body composition of the user, for example, at least one of body fat mass, body water mass, muscle mass, protein mass, and inorganic mass. Therefore, the body composition of the user may be analyzed from the information of the capacitance C of the sensing signal output from the second electrodes IE2.

In various exemplary embodiments, during the second mode, the processor 110 may control the touch panel 151 in a self-cap method. That is, the processor 110 may apply the driving current to the first electrode and/or the second electrode and receive the sensing signal output each of the first electrodes and/or each of the second electrodes to analyze the body composition based on the capacitance C between the first electrode and/or the second electrode and the body. The self-cap method may measure a more accurate change in the capacitance C for large area physical contact and may improve accuracy of the body composition analysis.

In various exemplary embodiments, the processor 110 may perform a correction on a value of the capacitance C determined from the sensing signal. For example, the processor 110 may correct the value of the capacitance C based on a temperature and/or a humidity of the temperature/humidity sensor 147 provided in the sensor module 140. Since the capacitance C generally increases as an operation temperature of a capacitor increases, the value of the capacitance C of the touch panel 151 may not be accurately measured when the terminal 100 operates at a high temperature. Therefore, the processor 110 may apply an arbitrary coefficient corresponding to a value of the temperature measured by the temperature/humidity sensor 147 to the value of the capacitance C determined from the sensing signal to correct the value of the capacitance C. Alternatively, for example, the processor 110 may correct a change in the value of the capacitance C by a protective film or the like attached to a surface of the terminal 100. Alternatively, for example, the processor 110 may correct the value of the capacitance C based on a parasitic effect, such as a low-ground mass effect, which may occur in the touch panel 151. The correction of the value of the capacitance C according to the disclosure is not limited to those described above.

In the above description, the terminal 100 measures the body composition using the coil antenna 171 for wireless charging. However, the exemplary embodiment is not limited thereto. That is, in various other exemplary embodiments, the terminal 100 may measure the body composition using other coil type antennas that may induce an electric field (or a magnetic field) in the vicinity, for example, the coil or the like provided in the RF antenna or the (digital) pen sensor 152, instead of the coil antenna 171 for wireless charging.

The terminal 100 may output the analyzed body composition to the user through the display 160 or the like. For example, the processor 110 may visually output the measured body composition in various forms such as a text, an image, an emoticon, a graph, and a table. Alternatively, the processor 110 may audibly output the measured body composition through a voice, a sound, or the like.

Figure 10:
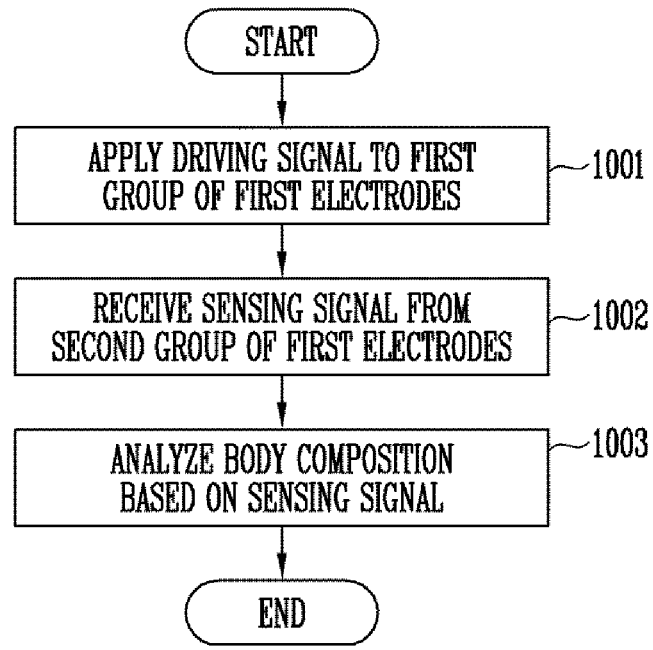
FIG. 10 is a flowchart of another exemplary embodiment of a method for controlling the terminal in the second mode shown in FIG. 7.
Figure 11:
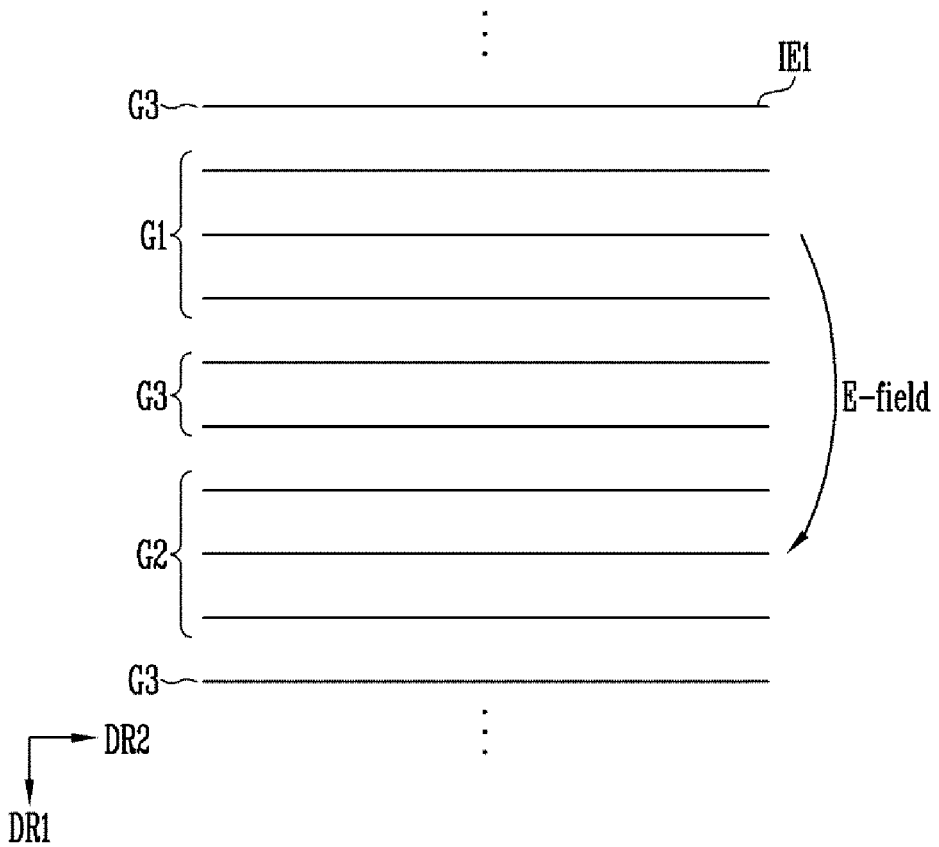
FIGS. 11, 12, and 13 are diagrams describing an exemplary embodiment of the method for controlling a terminal of FIG. 10.
Figure 12:
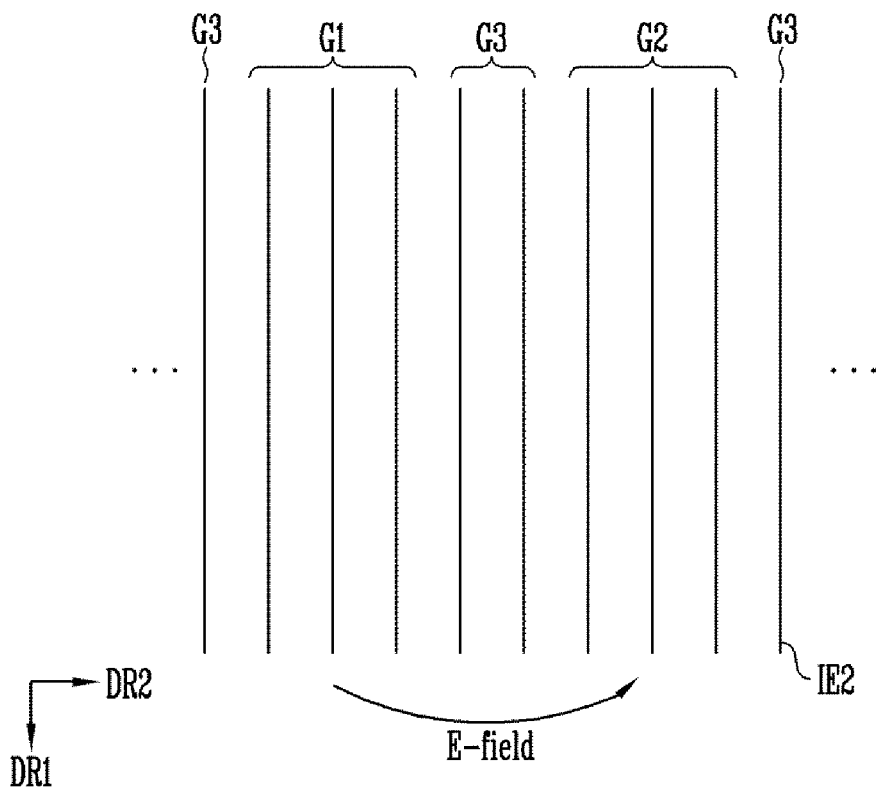
Figure 13:
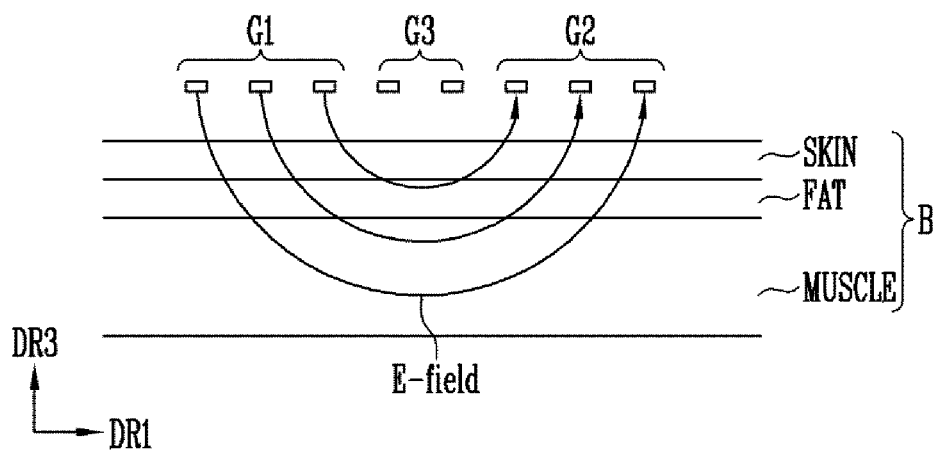

FIG. 10 is a flowchart of another exemplary embodiment of a method for controlling the terminal in the second mode shown in FIG. 7. FIGS. 11 to 13 are diagrams describing an exemplary embodiment of the method for controlling a terminal of FIG. 10. FIGS. 10 to 13 show a method of measuring the body composition using the touch screen panel.

Before operation in the second mode, that is, in the first mode, the processor 110 may sense the touch input using the first electrodes IE1 and the second electrodes IE2 of the touch panel 151. For example, the processor 110 may apply the driving current to the first electrodes IE1 and detect a generation position or the like of the touch input using the sensing signal output from the second electrodes IE2. That is, the first mode may correspond to a first period to sense the touch input of the user. As such, the first mode may be a sensing mode.

Referring to FIG. 10, in the second mode, the processor 110 may measure the body composition using any one of the first electrodes IE1 and the second electrodes IE2 of the touch panel 151. For example, the processor 110 may apply the driving signal to a first group G1 of the first electrodes IE1 as shown in FIG. 11 (1001). In another exemplary embodiment, the processor 110 may also apply the driving signal to a first group G1 of the second electrodes IE2 as shown in FIG. 12. That is, the second mode may correspond to a second period to measure the body composition of the user. As such, the second mode may be a measuring mode.

The first group G1 may include a part of the first electrodes IE1 provided in the touch panel 151. The first group G1 may include a plurality of first electrodes IE1 disposed adjacent to each other as a part of the first electrodes IE1.

The processor 110 may apply the driving current to the first electrodes IE1 included in the first group G1. In an exemplary embodiment, the driving current for the first group G1 may be performed simultaneously for the first electrodes IE1 included in the first group G1. Therefore, the first electrodes IE1 configuring the first group G1 may operate as one driving electrode having a large area.

In various exemplary embodiments, the drive current applied to the first group G1 during the second mode may be current of which a magnitude (or level) is smaller than the drive current applied to the touch panel 151 during the first mode and/or current of which a frequency lower than the drive current applied to the touch panel 151 during the first mode. Therefore, since an intensity of an electric field acting on the body of the user and/or current through the body of the user is reduced, an effect of the electric field and/or the current on the body of the user may be minimized.

When the driving current is applied to the first electrodes IE1 included in the first group G1, an electric field E-field may be formed between the first group G1 and the second group G2. The electric field E-field may act on a body B of the user approaching the terminal 100 as shown in FIG. 13 to induce the eddy current.

The processor 110 may receive the sensing signal output from the second group G2 of the first electrodes IE1 (1002). The second group G2 may include a portion other than the first group G1 of the first electrodes IE1 provided in the touch panel 151. The second group G2 may include a plurality of first electrodes IE1 disposed adjacent to each other except for the first group G1 of the first electrodes IE1.

The first group G1 and the second group G2 of the first electrodes IE1 may be set to be spaced apart from each other. That is, at least one other first electrode IE1 may be disposed between the first electrodes IE1 configuring the first group G1 and the first electrodes IE1 configuring the second group G2. Hereinafter, the first electrodes IE1 except for the first group G1 and the second group G2 are referred to as a third group G3.

During the second mode, the first electrodes IE1 configuring the third group G3 may be controlled to be ground electrodes or controlled to be floating electrodes. For example, the processor 110 may apply current corresponding to a ground voltage to the first electrodes IE1 of the third group G3 during the second mode. Here, the current applied to the first electrodes IE1 of the third group G3 may have a magnitude (or level) different from that of the driving current applied to the first electrodes IE1 of the first group G1.

Alternatively, for example, the processor 110 may not apply current to the first electrodes IE1 of the third group G3 during the second mode. In such an exemplary embodiment, the first electrodes IE1 of the third group G3 may be floated.

When the third group G3 that is grounded or floated is disposed between the first group G1 and the second group G2, separation between the first electrodes IE1 of the first group G1 and the first electrodes IE1 of the second group G2 may be better achieved. As a result, the electric field E-field between the first group G1 and the second group G2, and the capacitance C according to the electric field E-field may be measured more accurately. Furthermore, since the first group G1 and the second group G2 are sufficiently spaced apart from each other, the electric field E-field may have wide range to pass through muscle portions of the body B of the user.

Since the driving signals are simultaneously applied to the first electrodes IE1 of the first group G1, the processor 110 may simultaneously receive the sensing signals from the first electrodes IE1 of the second group G2. That is, the first electrodes IE1 configuring the second group G2 may operate as one sensing electrode having a large area.

The processor 110 may analyze the body composition of the user based on the sensed signal (1003).

The sensing signal includes the information of the capacitance C for the electric field E-field formed between the first electrodes IE1 of the first group G1 and the first electrodes IE1 of the second group G2. The capacitance C may vary according to an electrical characteristic of the body B of the user who is in contact with the touch screen panel and the electrical characteristic of the body B of the user may be determined according to the eddy current induced by the electric field of the first group G1. The eddy current may be varied based on the body composition of the user, for example, at least one of body fat mass, body water mass, muscle mass, protein mass, and inorganic mass. Therefore, the body composition of the user may be analyzed from the sensing signal output from the first electrodes IE1 of the second group G2.

In various exemplary embodiments, the processor 110 may perform a correction on a value of the capacitance C determined from the sensing signal. For example, the processor 110 may correct the value of the capacitance C based on a temperature and/or a humidity of the temperature/humidity sensor 147 provided in the sensor module 140. Since the capacitance C generally increases as an operation temperature of a capacitor increases, the value of the capacitance C of the touch panel 151 may not be accurately measured when the terminal 100 operates at a high temperature. Therefore, the processor 110 may apply an arbitrary coefficient corresponding to a value of the temperature measured by the temperature/humidity sensor 147 to the value of the capacitance C determined from the sensing signal to correct the value of the capacitance C. Alternatively, for example, the processor 110 may correct a change in the value of the capacitance C by a protective film or the like attached to a surface of the terminal 100. Alternatively, for example, the processor 110 may correct the value of the capacitance C based on a parasitic effect, such as a low-ground mass effect, which may occur in the touch panel 151. The correction of the value of the capacitance C according to the disclosure is not limited to those described above.

While the body composition is measured using the first electrode IE1, a driving signal may not be applied to the second electrodes IE2, and a sensing signal may not be output from the second electrodes IE2. Alternatively, while the body composition is measured using the first electrode IE1, the current corresponding to the ground voltage may be applied to the second electrodes IE2. However, the disclosure is not limited thereto.

The terminal 100 may output the analyzed body composition to the user through the display 160 or the like. For example, the processor 110 may visually output the measured body composition in various forms such as a text, an image, an emoticon, a graph, and a table. Alternatively, the processor 110 may audibly output the measured body composition through a voice, a sound, or the like.

Meanwhile, in the above description, the body composition is measured using the first electrodes IE1 of the touch panel 151. However, the exemplary embodiment is not limited thereto. That is, in various other exemplary embodiments, the body composition may be measured using the second electrodes IE2 of the touch panel 151 as shown in FIG. 12.

That is, the processor 110 may apply the driving signal to the first group G1 of the second electrodes IE2 during the second mode and analyze the body composition using the sensing signal output from the second group G2 of the second electrodes IE2. The third group G3 including at least one second electrode IE2 may be disposed between the first group G1 and the second group G2 of the second electrodes IE2. During the second mode, the current corresponding to the ground voltage may be applied to the second electrodes IE2 configuring the third group G3, or current may not be applied to the second electrodes IE2 configuring the third group G3.

While the processor 110 measures the body composition using the second electrodes IE2, a driving signal may not be supplied to the first electrodes IE1, or the current corresponding to the ground voltage may be applied to the first electrodes IE1.

In various exemplary embodiments, during the operation in the second mode, normal touch input sensing of the touch panel 151 may be interrupted. That is, during the second mode, the electrodes IE of the touch panel 151 may be driven so as to perform the body composition measurement as described above, and the position or the like of the touch input may not be sensed. However, the exemplary embodiment is not limited thereto, and in various other exemplary embodiments, the touch panel 151 may perform touch input sensing during the operation in the second mode. In such an exemplary embodiment, the touch panel 151 may be driven so as to perform the body composition measurement during the first period and perform the touch input sensing during the second period using a time division method. However, the exemplary embodiment is not limited thereto.

Figure 14:
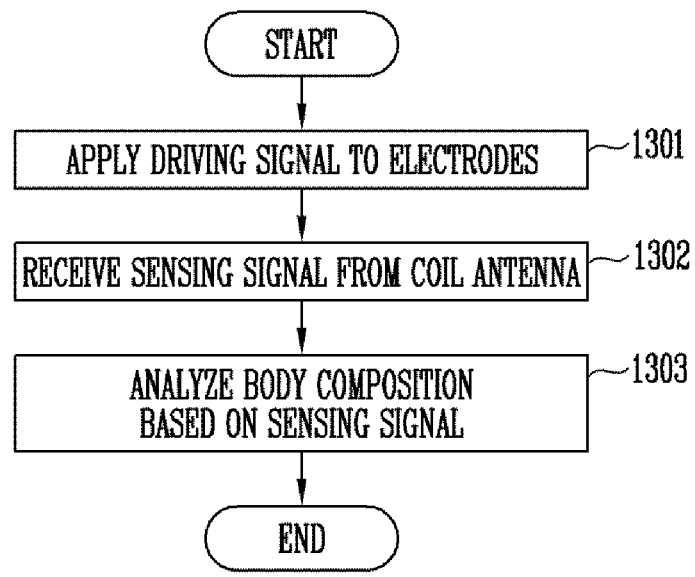
FIG. 14 is a flowchart of still another exemplary embodiment of a method for controlling the terminal in the second mode shown in FIG. 7.

FIG. 14 is a flowchart of still another exemplary embodiment of a method for controlling the terminal in the second mode shown in FIG. 7.

In FIG. 14, the touch screen panel forms the electric field in the vicinity and the coil antenna 171 outputs the sensing signal, instead the coil antenna 171 forms the electric field in the vicinity and the touch screen panel outputs the sensing signal in comparison with the exemplary embodiment of FIGS. 8 and 9. This will be described in detail as follows.

Referring to FIG. 9 together, before the operation in the second mode, that is, in the first mode, the coil antenna 171 may be electrically connected to the rectifier 172. The rectifier 172 may receive current induced to the coil antenna 171 and may pass current of a specific frequency band through resonance. The current output through the rectifier 172 may further be controlled through another control circuit or the like configuring the PMIC and may be supplied to a power demand such as the battery 180.

Although not shown, the rectifier 172 may be electrically further coupled to the processor 110.

In addition, in the first mode, the processor 110 may sense the touch input using the first electrodes IE1 and the second electrodes IE2 of the touch panel 151. For example, the processor 110 may apply the driving current to the first electrodes IE1 and detect the generation position or the like of the touch input using the sensing signal output from the second electrodes IE2.

Referring to FIG. 14, in the second mode, the processor 110 may apply the driving current to all or a part of the first electrodes IE1 and/or the second electrodes IE2 of the touch panel 151 (1301). The driving current applied to the electrodes IE in the second mode may be controlled to have a value of the intensity and/or frequency lower than the driving current applied to the electrodes IE in the first mode.

When the driving current is applied to all or a part of the first electrodes IE1 and/or the second electrodes IE2, the electric field may be formed around the touch panel 151. The electric field around the touch panel 151 may induce the eddy current to the body of the user approaching the terminal 100. An intensity and/or a direction of the electric field around the touch panel 151 may be changed by the eddy current of the body of the user.

The change in the electric field around the touch panel 151 may generate the induced electromotive force in the coil antenna 171. The rectifier 172 may receive the induced electromotive force generated in the coil antenna 171 and transfer the induced electromotive force to the processor 110. Here, a signal transferred to the processor 110 may be in a form of a sensing signal corresponding to the induced electromotive force generated in the coil antenna 171.

The processor 110 may receive the sensing signal based on the induced electromotive force of the coil antenna 171 through the rectifier 172 (1302), and may perform the body composition analysis based on the received sensing signal (1303).

Figure 15:
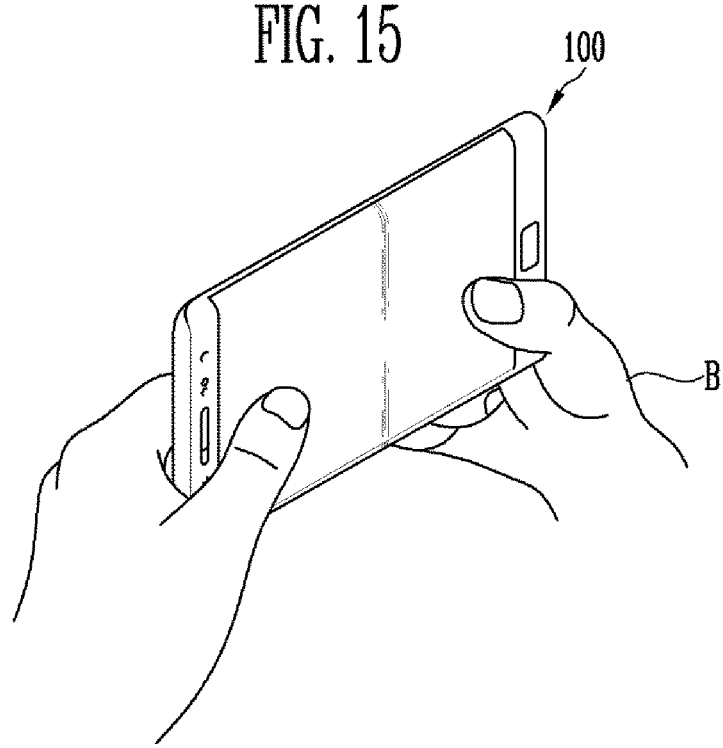
FIG. 15 illustrates an exemplary embodiment of a terminal constructed according to the principles of the invention.

FIG. 15 illustrates an exemplary embodiment of a terminal constructed according to the principles of the invention.

Referring to FIG. 15, the user of the terminal 100 may measure the body composition by touching a portion of the B (for example, a finger) to at least two points of the touch screen panel. Such an exemplary embodiment may be applied to the exemplary embodiment described with reference to FIGS. 10 to 12, but is not limited thereto, and such an exemplary embodiment may be applied to various other exemplary embodiments.

In the exemplary embodiment with reference to FIGS. 10 to 12, the terminal 100 may first detect the touch position of the body B, and set the electrodes IE corresponding to any one of at least two points at which the touch position is detected as the first group G1 and the electrodes IE corresponding to the other as the second group G2.

However, in another exemplary embodiment, the electrodes IE of the first group G1 and the electrodes of the second group G2 may be set in advance. In such an exemplary embodiment, the body B of the user is required to be in contact with the touch screen panel at a position corresponding to the electrodes IE included in the first group G1 and the electrodes IE included in the second group G2.

In order to induce the user to contact the body B at a correct position, at least one UI, GUI, or the like for guiding the touch point on the touch screen panel may be displayed.

Figure 16:
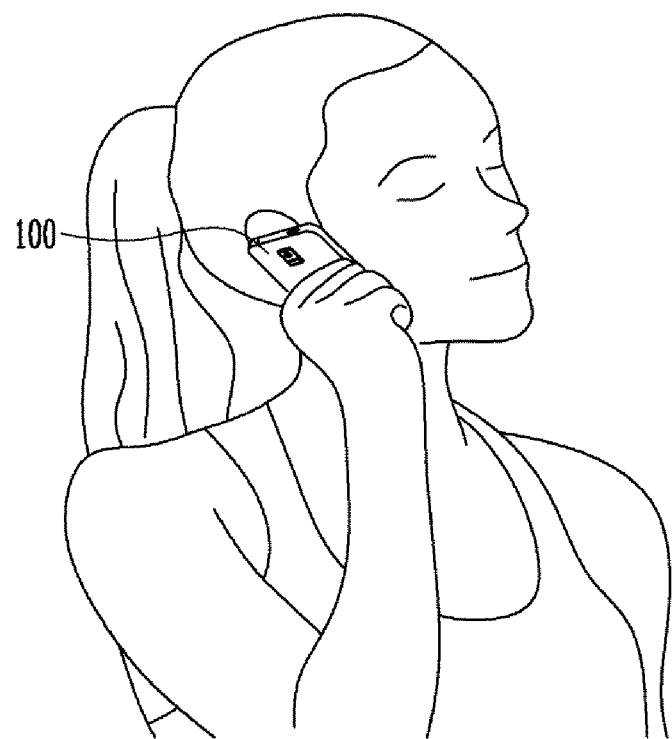
FIG. 16 illustrates another exemplary embodiment of a terminal constructed according the principles of the invention.

FIG. 16 illustrates another exemplary embodiment of a terminal constructed according to the principles of the invention.

Referring to FIG. 16, when the user performs a call using the terminal 100 or takes a gesture to perform a call, a large area of the touch screen panel may be in contact with the body of the user. In such an exemplary embodiment, the user may easily perform the body composition measurement simply by performing a call or taking an action of performing a call.

Figure 17:
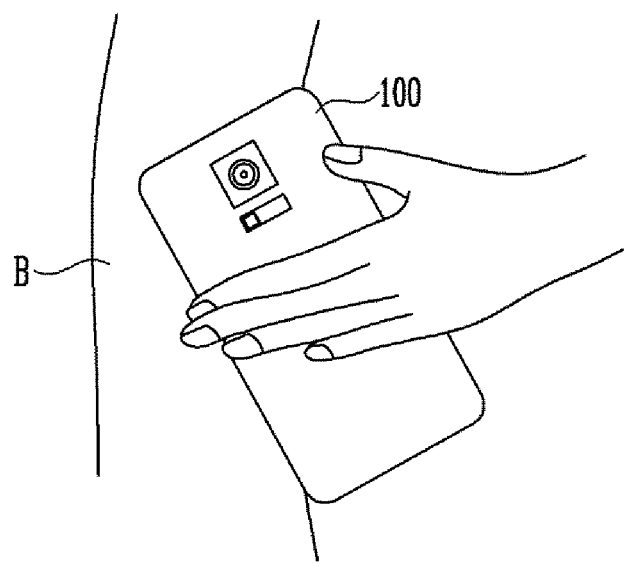
FIG. 17 illustrates still another exemplary embodiment of a terminal constructed according to the principles of the invention.

FIG. 17 illustrates still another exemplary embodiment of a terminal constructed according to the principles of the invention.

Referring to FIG. 17, the user may measure the body composition by contacting a portion of the body B with the entire surface of the touch screen panel of the terminal 100. A portion of the body B may include various portions such as, a wrist, a palm, an arm, an elbow, a thigh, a calf, a shoulder, a sole, a heel, an instep, an ankle, a waist, a back, an abdomen, a hip, a knee, a neck, a cheek, a chin, and a forehead.

Such an exemplary embodiment may be more suitably applied, for example, when the terminal 100 is a wearable device. For example, when the terminal 100 is implemented as a wearable device, the user may easily perform the body composition measurement by wearing the terminal 100 on a suitable portion of the body B. However, the disclosure is not limited thereto.

As described above, in the disclosure, since body composition measurement may be performed using the coil antenna 171 for wireless charging and the touch screen panel provided in the terminal 100, the body composition may be measured without adding a separate hardware configuration for the body composition measurement. In addition, in the disclosure, the body composition is measured using the coil antenna 171 and the electrodes IE of the touch panel 151, which are not exposed to the outside of the terminal 100 and are mounted in the terminal 100. Therefore, damage to beauty of the terminal due to an external electrode may be prevented, damage of the electrode for the body composition measurement may be prevented, and electric shock of the user due to an electrode exposed to the outside may be prevented.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A terminal comprising:
   a touch panel including first electrodes arranged in a first direction and second electrodes arranged in a second direction intersecting the first direction;
   a display panel attached to the touch panel and to display an image; and
   a processor to control the touch panel and the display panel,
   wherein, in a measuring mode, the processor is configured to:
   apply a driving signal to the touch panel, the touch panel being configured to form an electric field and/or magnetic field when the driving signal is applied, and
   determine body composition of a user based on a sensing signal output from the touch panel in accordance with eddy current, the eddy current being induced to a body of the user by the electric field and/or magnetic field formed around the touch panel,
   wherein, in a sensing mode, the processor is configured to apply the driving signal to the first electrodes and to sense a touch input based on the sensing signal output from the second electrodes, and
   wherein the processor is configured to operate in the sensing mode during a first period and, after the first period has elapsed, to operate in the measuring mode during a second period subsequent to the first period.

2. The terminal according to claim 1, wherein the processor is configured to apply the driving signal to a first group of the first electrodes and to receive the sensing signal from a second group of the first electrodes.

3. The terminal according to claim 2, wherein a third group of the first electrodes including at least one first electrode is disposed between the first group and the second group such that the first group and the second group are spaced apart from each other.

4. The terminal according to claim 3, wherein, in the measuring mode, the processor is configured to apply current corresponding to a ground voltage to the third group of the first electrodes, or does not apply current to the third group.

5. A method for controlling a terminal comprising a touch panel including first electrodes arranged in a first direction, and second electrodes arranged in a second direction intersecting the first direction, the method comprising the steps of:
   applying a driving signal to a first group of either the first electrodes or the second electrodes in a measuring mode;
   receiving a sensing signal from a second group of either the first electrodes or the second electrodes;
   determining a body composition of a user based on the sensing signal,
   determining whether a second period corresponding to the measuring mode has elapsed;
   applying the driving signal to one of the first electrodes and the second electrodes in a sensing mode when the second period has elapsed;
   receiving the sensing signal output from the other of the first electrodes and the second electrodes;
   determining whether a first period corresponding to sensing mode has elapsed; and
   returning to the measuring mode when the first period has elapsed.

6. The method according to claim 5, wherein a third group is disposed between the first group and the second group such that the first group and the second group are spaced apart from each other.

7. The method according to claim 6, wherein the step of applying the driving signal to the first group includes applying current corresponding to a ground voltage to the third group.

* * * * *